United States Patent
Stora

(10) Patent No.: US 7,226,901 B2
(45) Date of Patent: Jun. 5, 2007

(54) STABLE TRANSPARENT PERFUMING EMULSION

(75) Inventor: Thierry Stora, Sergy (FR)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 10/723,922

(22) Filed: Nov. 24, 2003

(65) Prior Publication Data

US 2004/0116323 A1    Jun. 17, 2004

Related U.S. Application Data

(63) Continuation of application No. PCT/IB02/01964, filed on May 29, 2002.

(30) Foreign Application Priority Data

Jun. 11, 2001    (WO) .................. PCT/IB01/01018
Jun. 14, 2001    (WO) .................. PCT/IB01/01047

(51) Int. Cl.
  *C11B 9/00*    (2006.01)
(52) U.S. Cl. ............................................. 512/1
(58) Field of Classification Search ................ 512/1

(56) References Cited

U.S. PATENT DOCUMENTS

| 6,403,109 B1 | 6/2002 | Stora ..................... 424/401 |
| 6,419,909 B1 * | 7/2002 | Lorant et al. ............... 424/59 |
| 6,573,235 B1 * | 6/2003 | Surbled et al. ............. 512/1 |
| 6,774,101 B2 * | 8/2004 | Stora et al. ................ 512/1 |

FOREIGN PATENT DOCUMENTS

| EP | 1 064 929 | 1/2001 |
| EP | 1 064 989 | 1/2001 |
| EP | 1 097 704 | 5/2001 |
| WO | WO 00/33804 | 6/2000 |
| WO | WO 01/13875 | 3/2001 |

* cited by examiner

*Primary Examiner*—Monique T. Cole
(74) *Attorney, Agent, or Firm*—Winston & Strawn LLP

(57) ABSTRACT

A particularly stable perfuming composition in the form of a transparent fluid water-in-oil or oil-in-water emulsion is obtained by addition of a substance to the oily phase, capable of bringing closer the densities of the respective dispersed and continuous phases.

20 Claims, No Drawings

STABLE TRANSPARENT PERFUMING EMULSION

CROSS-REFERENCE TO RELATED APPLICATIONS

This application is a continuation of International Application PCT/IB02/01964 filed May 29, 2002, the entire content of which is expressly incorporated herein by reference thereto.

TECHNICAL FIELD

The present invention relates to the field of perfumery. It concerns more particularly an alcohol-free perfuming composition in the form of a fluid, transparent water-in-oil or oil-in-water emulsion. The emulsion of the invention is characterised by an outstanding stability, the densities of the respective oily and aqueous phases being particularly close to one another.

BACKGROUND OF THE INVENTION

Several criteria must be met in a well-formulated emulsion. Two of the most readily apparent requirements are that the emulsion possesses adequate physical and chemical stability.

First of all, chemical stability of the various components of the emulsion should receive a particular attention in perfumery, since the main materials used in perfuming compositions, namely perfuming ingredients, are well-known to be particularly difficult to stabilise in formulations such as emulsions (Cosmetics and Toileteries® Magazine, Vol. 109, pages 71–75, 1994). The stabilisation of formulations comprising high fragrance levels such as those concerned by the present invention constitutes therefore a specific and challenging problem, notably different from that of the stabilisation of a cosmetic emulsion, which comprises other kinds of components, the nature of which is generally dependent on the type of the final cosmetic product (typical active ingredients include natural or synthetic oils, hydrocarbons, halogenated carbons, esters of mineral acids, silicones). Furthermore, such cosmetic compositions contain very low amounts of perfuming ingredients.

On the other hand, an essential requirement sought in the formulation of an emulsion of any kind is the physical stability, without which the emulsion will soon revert back to separate bulk phases. One typical phenomenon associated with physical instability is constituted by the upward and downward movement of dispersed droplets relative to the continuous phase, termed creaming or sedimentation respectively. The factors that influence the rate of sedimentation or creaming are the diameter of the suspended droplets, the viscosity of the suspending medium and the difference in densities between the dispersed phase and the dispersion medium.

The prior art discloses a first means to avoid this destabilisation phenomenon, consisting in reducing the particle size of the dispersed system, which contributes greatly toward overcoming or minimising creaming.

Therefore, perfuming compositions in the form of microemulsions are known from the prior art. Microemulsions are liquid dispersions of water and oil that are made homogeneous, transparent and stable by the addition of relatively large amounts of a surfactant and a co-surfactant. While emulsions are unstable, microemulsions are stable and, therefore, they are formed spontaneously when oil, water, surfactants and co-surfactants are mixed together. Conversely, emulsions require input of considerable mechanical energy for their preparation. Furthermore, microemulsion droplets have a narrow droplet size distribution with a mean diameter range of approximately 5–50 nm. Consequently this type of formulation scatters little light and is therefore transparent or at least translucent, while emulsions have very broad droplet size distributions and, as the emulsion droplets are comparable in size or larger than the wavelength of visible light, they scatter it more or less strongly depending on the difference in refractive index between oil and water. Thus most emulsions are opaque. It appears therefore that emulsions and microemulsions constitute two distinct dispersed systems, of different nature for the reasons hereabove mentioned.

Now, for the purpose of the present invention, it is not desirable to incorporate an important amount of surfactant relative to the amount of perfuming ingredients, as this limits considerably the amount of fragrance that can be incorporated in the mixture. Therefore, a microemulsion does not constitute a suitable dispersed system for the present invention, which has to be in the form of an emulsion.

Another known transparent dispersed system of this type is the nanoemulsion characterised by an average size of the oily phase droplets below ca. 30–75 nm. The droplets are small enough to make the emulsion translucent or partially transparent. Although these nanoemulsions present the advantage of needing lesser amount of surfactants than the microemulsions, they present nevertheless the disadvantage that their process of preparation is often difficult and delicate, and thus costly.

The other manner disclosed in the prior art to stabilise a conventional emulsion is the addition of a polymer to the dispersed phase. However, this solution presents the drawback of thickening said phase, thus increasing the viscosity of the emulsion such that it is no longer easily sprayable.

WO 00/33804, the entire content of which is hereby incorporated herein by reference and which describes a perfuming composition in the form of a transparent emulsion, already matches most of the criteria required for such an emulsion (transparency, fluidity). However, the emulsion described in that publication has now been improved in terms of physical stability, thanks to a novel solution to the physical stability problem described herein.

In fact, the invention now provides a transparent, fluid, water-in-oil or oil-in-water emulsion characterised by the fact that the densities of the respective continuous and dispersed phases have almost matching values. This solution to the well-known problem of physical instability, and more particularly of creaming and sedimentation, specifically adapted to a dispersed system of the emulsion type, has been achieved thanks to the presence of a specific additive in the oily phase of the emulsion, namely a volatile fluorinated oil having a density higher than 1.

This class of compounds has already been used in some kinds of emulsions. In particular, EP 1064929 discloses the use of such a volatile fluorinated oil in a cosmetic composition for attenuating skin deficiencies and for giving a matt skin appearance. The cosmetic composition there-disclosed is not only totally distinct, from a formulation point of view, from a perfuming composition, but also the fluorinated oil is used in this prior art for a technical effect consisting in modifying the skin appearance, thus an aim distinct from that achieved by the present invention, i.e. the stabilisation of an emulsion.

EP 1064989 also discloses a cosmetic emulsion comprising a volatile fluorinated oil. Once again, the latter is described as being useful for its topical properties in such cosmetic applications, providing compositions of easy application, as well as fresh and soft products. Moreover, this document specifies that the fluorinated oil is very difficult to stabilise and may provoke an instability phenomenon such as foaming, demixing and changes in viscosity, and that it has thus to be used in combination with a specific surfactant, able to stabilise the emulsion. According to the teaching of this document, a volatile fluorinated oil is thus very difficult to stabilise.

The present invention now seeks to resolve these deficiencies.

SUMMARY OF THE INVENTION

The present invention, in a totally unexpected manner considering the teaching of the prior art, discloses that a perfuming composition, in the form of an emulsion, can be advantageously stabilised by minimising the difference existing between the densities of the respective continuous and dispersed phases and that such an effect could be achieved by adding to the oily phase of the emulsion a volatile fluorinated oil having a density higher than one, without any need of combining that ingredient with a specific surfactant such as disclosed in EP 1064989. Together with the transparency, fluidity and stability requirements, the composition of the invention is also alcohol-free, which is an advantage henceforth sought in such formulations.

The present invention provides an alcohol free perfuming composition in the form of a transparent water-in-oil or oil-in-water emulsion having an outstanding stability. In this composition, the difference between the density of the oily phase and that of the aqueous phase in less than or equal to 0.007, and preferably is less than or equal to 0.005. These emulsions are advantageously particularly resistant to phenomena such as creaming and sedimentation and constitutes a novel, effective solution to the instability problems known in the prior art compositions.

DETAILED DESCRIPTION OF THE PREFERRED EMBODIMENTS

According to the invention, it has been established that a substance can be added to a perfuming composition which is an emulsion and provide the technical effect of bringing closer the densities of the respective phases of this emulsion. A volatile fluorinated oil having a density higher than 1 constitutes such a substance. Also, the invention provides a perfuming composition in the form of an emulsion, wherein the oily phase comprises a certain amount of a volatile fluorinated oil having a density higher than 1. And furthermore, the invention also concerns the use of that ingredient as a stabilisation agent in an emulsion.

The perfuming composition of the invention is in the form of a transparent water-in-oil or oil-in-water emulsion susceptible of being sprayed, comprising an aqueous phase and an oily phase containing at least 3% by weight of perfuming ingredients relative to the total weight of the composition, wherein the difference between the density of the oily phase and that of the aqueous phase is less than or equal to 0.007, preferably less than or equal to 0.005. This technical effect may be achieved when the oily phase contains a volatile fluorinated oil having a density higher than 1.

What is intended here by perfuming composition is a perfume vehicle, the main function of which is to impart, enhance or modify the odoriferous properties of a product.

In the case of an oil-in-water emulsion, the continuous phase is formed by water (aqueous phase) and the dispersed phase is formed by the oil (oily phase) which is essentially formed of perfuming ingredients. Conversely, the emulsion is a water-in-oil or inverse emulsion when the continuous phase is formed by the oil wherein the water is dispersed. The latter type of emulsion is preferred according to one embodiment of the invention.

As mentioned above, the emulsion according to the present invention meets a certain number of criteria required in the field of perfumery, for applications such as perfumes, eaux de toilette, or Colognes.

First of all, the composition of the invention is alcohol free. There is at present a demand for such types of compositions, particularly from consumers with sensitive skins or whose skins are often exposed to the sun.

Moreover, the composition of the invention is fluid, or in other words susceptible of being sprayed. In particular, its viscosity is lower than 10 Pa.s, independently of the nature of the emulsion.

Furthermore, the emulsion is transparent, a desirable quality in the field of perfumery. The transparency is achieved thanks to the addition to the perfuming compositions of ingredients capable of modifying the refractive indices of the two phases, so as to form a transparent emulsion. The particular solid or liquid ingredients used to act either on the oily or on the aqueous phase in order to achieve transparency are described in WO 00/33804, the entire content of which is expressly included by reference herein, namely as regards the citation of such ingredients. Also, the refractive index of a finished perfuming composition according to the invention has a value between ca. 1.40 and 1.44.

Now, besides all the mentioned criteria already met, the present invention brings an advantageous improvement to the known transparent emulsions. In fact, it has been discovered that the addition of a certain ingredient to the oily phase of the emulsion could significantly improve the physical stability of the emulsion, in particular with regard to the creaming and sedimentation problems. In particular, the addition of such an ingredient to the oily phase of the emulsion makes it possible to narrow the difference between the respective densities of the two phases, so as to bring it within the limit defined above, namely lower or equal to 0.007, or even 0.005 in the preferred embodiments. The invention brings thus a novel solution to the known problem of physical stability, by providing means for acting on the relative densities of both phases.

It has been observed that in the context of this invention it is possible to use a certain number of substances or agents having the capacity of acting on the oily phase as desired and the choice of which depends on individual criteria that can be easily established by the skilled person for each composition. The above-mentioned agent which will be used to act on the oily phase must be soluble in the latter.

Preferably the agent is chosen with a density higher than 1. It has been discovered that the desired above-described technical effect could be advantageously achieved in particular by adding to the oily phase a volatile fluorinated oil having a density higher than 1. The technical effect obtained with this compound is particularly surprising considering that, amongst the prior art, EP 1064989 teaches the need to combine that ingredient with a particular surfactant in order to stabilise it in an emulsion.

Preferably, the fluorinated oil used according to the present invention is selected from the group consisting of hydrofluoroethers such as methoxynonafluorobutane or ethoxynonafluorobutane. In a particular embodiment the ingredient added to the oily phase of the emulsion is methoxynonafluorobutane. The volatile fluorinated oil may also be used in mixture with a less volatile fluorinated oil such as a perfluoroalcane. Perfluorodecaline is an example of a suitable perfluoroalcane for this purpose. The amount of fluorinated oil added to the oily phase is comprised between 5 and 50% by weight relative to the oily phase.

The emulsions of the invention can contain from 5 to 50% by weight, preferably from 10 to 35% by weight, of dispersed phase and from 50 to 95% by weight, preferably 65 to 90% by weight, of continuous phase. These values are relative to the total weight of the emulsion and are independent of the fact that the compositions of the invention are in the form of a water-in-oil or an oil-in-water emulsion.

The oily phase is essentially formed of perfuming ingredients. Typically it comprises from 15 to 60%, preferably from 20 to 50% by weight of perfuming ingredients. The aqueous phase comprises from 20 to 65% of water.

Optionally, the composition of the invention may further contain at least one surfactant. This surfactant will be used in a proportion of 0 to 8%, preferably 0.1 to 5% by weight, relative to the total weight of the emulsion. The best results were obtained using 2 to 5% by weight of surfactant.

Different types of surfactants can be used in the context of the invention. One can mention the non-ionic, cationic, anionic, amphoteric surfactants and the phospholipids, which may all be used in the present invention. Preferably, there is used a non-ionic surfactant or a mixture of two non-ionic surfactants. As non restrictive examples, the ethoxylated nonylphenol comprising 9 to 10 units of ethyleneglycol (on sale under the name of Triton® N-101; origin: Fluka, Switzerland) or the ethoxylated undecanol comprising 8 units of ethyleneglycol (on sale under the name of Imbentin® 0800; origin: Kolb AG, Switzerland) can be cited. Other examples include the surfactants known under the tradename Tween® (origin: ICI, England), such as Tween® 20 [polyoxyethylene (20) sorbitan monolaurate], Tween® 40 [polyoxyethylene (20) sorbitan monopalmitate], Tween® 60 [polyoxyethylene (20) sorbitan monostearate] and Tween® 80 [polyoxyethylene (20) sorbitan monooleate], and the surfactants commercialised under the name of Span® (origin: ICI, England), such as Span® 20 (sorbitan monolaurate), Span® 40 (sorbitan monopalmitate), Span® 60 (sorbitan monostearate), and Span® 80 (sorbitan monooleate). One can further mention Cremophor® RH40 and RH60 (origin: BASF AG, Germany, which are ethoxylated hydrogenated ricin oils), Genapol® [origin: Hoechst AG, Germany, a sodium (alcohol polyglycol ether) laurylsulfate], the surfactant known under the name of Poloxamer® 407 (a diblock copolymer of ethyleneoxyde and propyleneoxyde, also commercialised under the names of Pluronic® F 127 and Pluracare® F 127, origin: BASF AG, Germany); Tetronic® (origin: BASF AG, Germany); DC 3225 C, DC 5200, DC 193 (origin: Dow Corning, USA); Abil® Em 97 (origin: Goldschmidt).

The perfuming ingredients that can be used in the present invention are all the ingredients commonly used in perfumery. These ingredients shall not be described in greater detail here, as their description cannot be exhaustive and the skilled person is able to choose them using his general knowledge and as a function of the desired olfactory effect. These perfuming ingredients belong to a variety of chemical classes, as varied as alcohols, aldehydes, ketones, esters, ethers, acetates, nitriles, terpernic hydrocarbons, heterocyclic nitrogen- or sulfur-containing compounds, as well as essential oils of natural and synthetic origin. Many of these ingredients are furthermore described in reference textbooks such as the book of S. Arctander, Perfume and Flavour Chemicals, 1969, Montclair, N.J., USA, or its more recent versions, or other books of similar nature. The nature of the perfuming ingredients is not an essential parameter of the invention, and the choice of the latter shall be solely dictated by hedonic requirements, i.e., as a function of the fragrance or odorant effect that it is desired.

The emulsion of the invention can be easily prepared by conventional mixing and homogenising methods, which therefore do not require a more detailed description herein. According to the present invention, emulsions are created with an average drop size above 200 nm, preferably below 1 µm.

EXAMPLES

The invention will now be illustrated by the following non-restrictive examples, in which the temperatures are indicated in degrees Celsius, the proportions of the ingredients are given in % by weight and the abbreviations have the usual meaning in the art.

Example 1

Preparation of an Alcohol-free Perfuming Composition in the Form of a Water-in-Oil Emulsion A water-in-oil emulsion containing a perfuming base has been prepared with the below-specified ingredients. Incorporation of the fluorinated oil was done after emulsification of the other ingredients by a current method in the art.

| Ingredients | Parts by weight |
| --- | --- |
| Perfuming base* | 10.00 |
| Silicon DC ® 345[1] | 43.00 |
| Methoxynonafluorobutane[2] | 15.00 |
| Water | 16.45 |
| 1,2-Butanediol | 11.55 |
| Abil ® Em 97[3] | 4.00 |
| Total | 100.00 |

[1] origin: Dow Corning
[2] origin: 3M
[3] origin: Goldschmidt

*The perfuming base was obtained by mixing the following ingredients:

| Ingredients | Parts by weight |
| --- | --- |
| Citronellyl acetate | 3 |
| Geranyl acetate | 9 |
| Linalyl acetate | 276 |
| 10% * Aldehyde C10 | 3 |
| 10% * Aldehyde C12 | 12 |
| Methyl anthranilate | 16 |
| Bergamot essential oil | 226 |
| Cetalox ®[1] | 5 |
| Lemon essential oil | 318 |
| Dihydromyrcenol[2] | 60 |
| Dipropyleneglycol | 20 |
| 10% * Elemi[3] | 20 |
| Fleuria 41063 B[4] | 3 |
| Ethyl linalol | 66 |
| 10% * 3-(4-Methoxyphenyl)-2-methylpropanal[4] | 30 |
| Geraniol | 6 |
| 50% * Habanolide ®[5] | 130 |

-continued

| Ingredients | Parts by weight |
|---|---|
| Hedione ®[6] | 215 |
| Hedione ®HC[7] | 72 |
| 10% ** Indol | 12 |
| Iso E Super[8] | 85 |
| Lavandin grosso essential oil | 26 |
| 1% * Liffarome ®[9] | 20 |
| Linalol | 40 |
| Sfuma madarin essential oil | 5 |
| 10% * Crinkled mint essential oil | 30 |
| Bigarade Neroli essential oil | 130 |
| Portugal Florida orange essential oil | 80 |
| Phenethylol | 9 |
| Petitgrain essential oil | 63 |
| Pipol | 5 |
| Rosemary essential oil | 16 |
| Terpineol | 9 |
| Violet essential oil | 50 |
| 1% * Zestover[10] | 30 |
| Total | 2100 |

* in dipropyleneglycol (DIPG)
** in triethanolamine
[1] 8,12-epoxy-13,14,15,16-tetranorlabdane; origin: Firmenich SA, Geneva, Switzerland
[2] origin: International Flavours and Fragrances, USA
[3] 5-allyl-1,2,3-trimethoxybenzene; origin: Calchauvet, Grasse, France
[4] origin: Firmenich SA, Geneva, Switzerland
[5] pentadecenolide; origin: Firmenich SA, Geneva, Switzerland
[6] Methyl dihydrojasmonate; origin: Firmenich SA, Geneva, Switzerland
[7] Methyl dihydrojasmonate with high content of isomer cis; origin: Firmenich SA, Geneva, Switzerland
[8] 1-(octahydro-2,3,8,8-tetramethyl-2-naphtalenyl)-1-ethanone; origin: International Flavours and Fragrances, USA
[9] 3-hexenyl methyl carbonate; origin: International Flavours and Fragrances, USA
[10] 2,4-dimethyl-3-cyclohexene-1-carbaldehyde The density of each of the two phases of the composition was measured at 30° on a density meter (DMA 4500; Anton Paar). The density of the aqueous phase was 1.0209 and that of the oily phase was 1.0249, thus forming a stable transparent emulsion.

Moreover, the respective refractive index of each phase was also measured and the difference between the two phases was of 0.0058.

Example 2

Preparation of an Alcohol-free Perfuming Composition in the Form of a Water-in-Oil Emulsion A water-in-oil emulsion containing a perfuming base has been prepared with the below-specified ingredients. Incorporation of the fluorinated oil was done after emulsification of the other ingredients by a current method in the art.

| Ingredients | Parts by weight |
|---|---|
| Perfuming base* | 10.00 |
| Silicon DC ® 345[1] | 45.00 |
| Methoxynonafluorobutane[2] | 13.00 |
| Water | 15.15 |
| 1,2-Butanediol | 12.85 |
| Abil ® Em 97[3] | 4.00 |
| Total | 100.00 |

[1] origin: Dow Corning
[2] origin: 3M
[3] origin: Goldschmidt

*The perfuming base was obtained by mixing the following ingredients:

| Ingredients | Parts by weight |
|---|---|
| Benzyl acetate | 250 |
| Pipol acetate | 70 |
| Styrallyl acetate | 230 |
| Phenylacetic aldehyde | 10 |
| Ambrettolide ®[1] | 10 |
| Astrotone | 300 |
| Bergamot essential oil | 1160 |
| β-Ionone | 550 |
| Cassis essential oil | 150 |
| 50% * Cetalox ®[2] | 60 |
| Lemon essential oil | 850 |
| Citronellol | 210 |
| Damascenone | 20 |
| 4-Decanolide | 20 |
| Dihydromyrcenol[3] | 440 |
| Dipropyleneglycol | 20 |
| Ethyl linalol | 720 |
| 7-Methyl-2H,4H-1,5-benzodioxepin-3-one[4] | 100 |
| Floralozone ®[5] | 50 |
| 3-(4-Methoxyphenyl)-2-methylpropanal[4] | 170 |
| Fructone ®[6] | 100 |
| Galbex ®[4] | 50 |
| γ-Damascone | 5 |
| Geranium essential oil | 30 |
| Grapefruit essential oil | 100 |
| Habanolide ®[7] | 1120 |
| Hedione ®[8] | 2890 |
| Hedione ® HC[9] | 950 |
| Heliopropanal[10] | 400 |
| Indol | 35 |
| Iso E Super[11] | 380 |
| Lavender grosso essential oil | 40 |
| Liffarome ® [12] | 1 |
| Lilial ®[13] | 1050 |
| Lyral ®[14] | 430 |
| Sfuma mandarin essential oil | 270 |
| Melonal[15] | 3 |
| Crinkled mint essential oil | 20 |
| Peony 434017[4] | 60 |
| Peony white HS 100001[4] | 200 |
| Phenethylol | 80 |
| Phenylhexanol | 50 |
| Pipol | 20 |
| Orange essential oil | 500 |
| Rosalva[16] | 4 |
| Benzyl salicylate | 400 |
| Pipol salicylate | 400 |
| 10% ** BHT[17] | 200 |
| Zestover[18] | 22 |
| Total | 15200 |

* in 2-(2-ethoxyethoxy)-1-ethanol
** in propyleneglycol
[1] origin: Givaudan-Roure SA, Vernier, Switzerland
[2] 8,12-epoxy-13,14,15,16-tetranorlabdane; origin: Firmenich SA, Geneva, Switzerland
[3] origin: International Flavours and Fragrances, USA
[4] origin: Firmenich SA, Geneva, Switzerland
[5] 3-(4-ethylphenyl)-2,2-dimethylpropanal + 3-(2-ethylphenyl)-2,2-dimethylpropanal; origin: International Flavours and Fragrances, Switzerland
[6] 2-methyl-1,3-dioxalane-2-ethylacetate; origin: International Flavours and Fragrances, USA
[7] pentadecenolide; origin: Firmenich SA, Geneva, Switzerland
[8] methyl dihydrojasmonate; origin: Firmenich SA, Geneva, Switzerland
[9] methyl dihydrojasmonate with high content of isomer cis; origin: Firmenich SA, Geneva, Switzerland
[10] 3-(1,3-benzodioxol-5-yl)-2-methylpropanal; origin: Firmenich SA, Geneva, Switzerland -continued

| Ingredients | Parts by weight |
|---|---|

[11] 1-(octahydro-2,3,8,8-tetramethyl-2-naphtalenyl)-1-ethanone; origin: International Flavours and Fragrances, USA
[12] 3-hexenyl-methyl carbonate; origin: International Flavours and Fragrances, USA
[13] 3-(4-tert-butylphenyl)-2-methylpropanal; origin: Givaudan-Roure SA, Vernier, Switzerland
[14] 4-(4-hydroxy-4-methylpentyl)-3-cyclohexen-1-carbaldehyde + 3-(4-hydroxy-4-methylpentyl)-3-cyclohexene-1-carbaldehyde; origin: International Flavours and Fragrances, USA
[15] 2,6-dimethyl-5-heptanal; origin: Givaudan-Roure SA, Vernier, Switzerland
[16] 9-decen-1-ol; origin: International Flavours and Fragrances, USA
[17] 2,6-di-tert-butyl-4-hydroxytoluene
[18] 2,4-dimethyl-3-cyclohexene-1-carbaldehyde; origin: Firmenich SA, Geneva, Switzerland The density of each of the two phases of the composition was measured at 30° on a density meter (DMA 4500; Anton Paar). The density of the aqueous phase was 1.0193 and that of the oily phase was 1.0218, thus forming a stable transparent emulsion.

Moreover, the respective refractive index of each phase was also measured and the difference between the two phases was of 0.0086.

Example 3

Preparation of an Alcohol-free Perfuming Composition in the Form of a Water-in-Oil Emulsion A water-in-oil emulsion containing the same perfuming base as that used in Example 1 has been prepared with the below-specified ingredients. Incorporation of the fluorinated oil was done after emulsification of the other ingredients by a current method in the art.

| Ingredients | Parts by weight |
|---|---|
| Perfuming base* | 10.00 |
| Silicon DC ® 345[1] | 41.20 |
| Ethoxynonafluorobutane[2] | 16.80 |
| Water | 17.00 |
| 1,2-Butanediol | 11.00 |
| Abil ® Em 97[3] | 4.00 |
| Total | 100.00 |

*see Example 1
[1] origin: Dow Corning
[2] origin: 3M
[3] origin: Goldschmidt

The density of each of the two phases of the composition was measured at 30° on a density meter (DMA 4500; Anton Paar). The density of the aqueous phase was 1.2010 and that of the oily phase was 1.0267 thus forming a stable transparent emulsion.

Moreover, the respective refractive index of each phase was also measured and the difference between the two phases was of 0.0023.

Example 4

Preparation of an Alcohol-free Perfuming Composition in the Form of a Water-in-Oil Emulsion A water-in-oil emulsion containing the same perfuming base as that used in Example 1 has been prepared with the below-specified ingredients. Incorporation of the fluorinated oil was done after emulsification of the other ingredients by a current method in the art.

| Ingredients | Parts by weight |
|---|---|
| Perfuming base* | 10.00 |
| Silicon DC ® 345[1] | 42.90 |
| Methoxynonafluorobutane[2] | 15.10 |
| Water | 16.45 |
| 1,3-Butanediol | 11.55 |
| Abil ® Em 97[3] | 4.00 |
| Total | 100.00 |

*see Example 1
[1] origin: Dow Corning
[2] origin: 3M
[3] origin: Goldschmidt

The density of each of the two phases of the composition was measured at 30° on a density meter (DMA 4500; Anton Paar). The density of the aqueous phase was 1.0201 and that of the oily phase was 1.0265, thus forming a stable transparent emulsion.

Moreover, the respective refractive index of each phase was also measured and the difference between the two phases was of 0.0090.

What is claimed is:

1. An alcohol free perfuming composition in the form of a transparent water-in-oil or oil-in-water emulsion capable of being sprayed, comprising an aqueous phase and an oily phase containing at least 3% by weight of perfuming ingredients relative to the total weight of the composition, wherein the difference between the density of the oily phase and that of the aqueous phase is less than or equal to 0.007, wherein the oily phase of the emulsion comprises a volatile fluorinated oil having a density higher than 1.

2. The perfuming composition according to claim 1, wherein the oily phase comprises from 5 to 50% by weight of the volatile fluorinated oil.

3. The perfuming composition according to claim 1, wherein the volatile fluorinated oil is a hydrofluoroether.

4. The perfuming composition according to claim 3, wherein the volatile fluorinated oil is methoxynonafluorobutane.

5. A perfuming composition according to claim 1, in the form of a perfume, an eau de toilette or a Cologne.

6. A process for the preparation of a perfuming composition, which comprises adding a volatile fluorinated oil having a density higher than 1 to an oily phase of an emulsion after an emulsification with an aqueous phase of the emulsion, wherein the difference between the density of the oily phase and that of the aqueous phase is less than or equal to 0.007 and at least 3% by weight of perfuming ingredients are present relative to the total weight of the composition.

7. A perfuming composition obtained by the process of claim 6.

8. A perfuming composition according to claim 7, in the form of a perfume, an eau de toilette or a Cologne.

9. The perfuming composition according to claim 1, wherein the oily phase includes therein an oil-soluble agent having a higher density than the oil.

10. The perfuming composition according to claim 1, wherein the difference between the density of the oily phase and that of the aqueous phase in less than or equal to 0.005.

11. The perfuming composition according to claim 1, wherein the viscosity of the emulsion is below 10 Pa.s.

12. The perfuming composition according to claim 1, in the form of a water-in-oil emulsion.

13. The perfuming composition according to claim 12, comprising from 50 to 95% by weight of oily phase and from 5 to 50% by weight of aqueous phase.

14. The process of claim 6, wherein the oily phase comprises from 5 to 50% by weight of the volatile fluorinated oil.

15. The process of claim 6, wherein the volatile fluorinated oil is a hydrofluoroether.

16. The process of claim 6, wherein the volatile fluorinated oil is methoxynonafluorobutane.

17. The process of claim 6, wherein the difference between the density of the oily phase and that of the aqueous phase in less than or equal to 0.005.

18. The process of claim 6, wherein the viscosity of the emulsion is below 10 Pa.s.

19. The process of claim 6, wherein the emulsion is in the form of a water-in-oil emulsion.

20. The process of claim 19, wherein the emulsion comprises from 50 to 95% by weight of oily phase and from 5 to 50% by weight of aqueous phase.

* * * * *

UNITED STATES PATENT AND TRADEMARK OFFICE
CERTIFICATE OF CORRECTION

| | |
|---|---|
| PATENT NO. | : 7,226,901 B2 |
| APPLICATION NO. | : 10/723922 |
| DATED | : June 5, 2007 |
| INVENTOR(S) | : Stora |

Page 1 of 1

It is certified that error appears in the above-identified patent and that said Letters Patent is hereby corrected as shown below:

Column 11:
Line 8 (claim 10, line 2), after "and that of the aqueous phase", delete "in" and insert -- is --.

Column 12:
Line 8 (claim 17, line 3), after "phase", delete "in" and insert -- is --.

Signed and Sealed this

Twenty-fourth Day of July, 2007

JON W. DUDAS
*Director of the United States Patent and Trademark Office*